US012685553B2

(12) United States Patent
O'Shea et al.

(10) Patent No.: US 12,685,553 B2
(45) Date of Patent: Jul. 21, 2026

(54) CUTTING ASSEMBLY AND A DRIVE ASSEMBLY FOR A SURGICAL INSTRUMENT

(71) Applicant: Stryker European Operations Limited, Carrigtwohill (IE)

(72) Inventors: Conor O'Shea, Innishannon (IE); Jonathan Browne, Dublin (IE); Emma O'carroll, Parteen (IE); Adrian Paul O'Heney, Cork (IE); Colin Langan, Midleton (IE); Alan Peter Whitford, Drogheda (IE); Damian Michael Curtin, Kerry (IE)

(73) Assignee: Stryker European Operations Limited, Carrigtwohill (IE)

( * ) Notice: Subject to any disclaimer, the term of this patent is extended or adjusted under 35 U.S.C. 154(b) by 554 days.

(21) Appl. No.: 17/923,755

(22) PCT Filed: May 6, 2021

(86) PCT No.: PCT/IB2021/053861
§ 371 (c)(1),
(2) Date: Nov. 7, 2022

(87) PCT Pub. No.: WO2021/224862
PCT Pub. Date: Nov. 11, 2021

(65) Prior Publication Data
US 2023/0190323 A1      Jun. 22, 2023

Related U.S. Application Data

(60) Provisional application No. 63/021,141, filed on May 7, 2020.

(51) Int. Cl.
*A61B 17/32*           (2006.01)

(52) U.S. Cl.
CPC ........ *A61B 17/32* (2013.01); *A61B 2217/005* (2013.01); *A61B 2217/007* (2013.01)

(58) Field of Classification Search
None
See application file for complete search history.

(56) References Cited

U.S. PATENT DOCUMENTS 4,492,574 A * 1/1985 Warrin ..................... A61C 1/07
                                                            433/81
5,792,167 A     8/1998 Kablik et al.
                    (Continued)

FOREIGN PATENT DOCUMENTS

WO           8101363 A1     5/1981
WO        2010098809 A2     9/2010
WO     WO-2017163226 A1 *   9/2017 ....... A61B 17/32002

OTHER PUBLICATIONS

Partial International Search Report for Application No. PCT/IB2021/053861 dated Aug. 5, 2021, 2 pages.
                    (Continued)

*Primary Examiner* — Martin T Ton
(74) *Attorney, Agent, or Firm* — Howard & Howard Attorneys PLLC

(57) ABSTRACT

A cutting assembly for a surgical instrument including an outer hub, an outer tube, a cutting implement, and a drive hub. A retention flange of the drive hub is arranged to retain the cutting shaft within the outer tube. The cutting assembly may include a seal, and the retention flange may contact the seal. An irrigation spacer may provide a stop of distal axial movement of the drive hub for permitting fluid to flow through irrigation passageways. The drive assembly may include an irrigation port and a suction port with a proximal end of the irrigation port may positioned axially distal to a proximal portion of the suction port. The irrigation port may be coupled to a handpiece, and the suction port may be
                    (Continued)

coupled to a back cap. A handpiece may include a saddle region, recesses, and/or an apex region to facilitate ergonomic handling of the surgical instrument.

19 Claims, 8 Drawing Sheets

(56) References Cited

U.S. PATENT DOCUMENTS

| | | | |
|---|---|---|---|
| 6,689,146 B1 | 2/2004 | Himes | |
| 7,144,383 B2 | 12/2006 | Arnett et al. | |
| 7,237,990 B2 | 7/2007 | Deng | |
| 7,318,831 B2 * | 1/2008 | Alvarez | A61B 17/32002 |
| | | | 606/180 |
| 7,473,263 B2 | 1/2009 | Johnston et al. | |
| 8,109,956 B2 | 2/2012 | Shadeck | |
| 8,277,474 B2 | 10/2012 | Norman et al. | |
| 8,475,481 B2 | 7/2013 | Himes | |
| 2004/0059363 A1 | 3/2004 | Alvarez et al. | |
| 2009/0228030 A1 | 9/2009 | Shadeck | |
| 2010/0324577 A1 | 12/2010 | Dunn | |
| 2011/0301578 A1 * | 12/2011 | Muniz-Medina | A61B 90/92 |
| | | | 606/1 |
| 2013/0018401 A1 * | 1/2013 | Deng | A61B 90/98 |
| | | | 606/170 |
| 2016/0106453 A1 * | 4/2016 | Deeny | A61B 17/32002 |
| | | | 606/170 |
| 2016/0235468 A1 | 8/2016 | Prisco et al. | |
| 2019/0223898 A1 | 7/2019 | Curtin et al. | |
| 2020/0146702 A1 | 5/2020 | Cushen et al. | |

OTHER PUBLICATIONS

International Search Report for Application No. PCT/IB2021/053861 dated Sep. 27, 2021, 3 pages.

* cited by examiner

CUTTING ASSEMBLY AND A DRIVE ASSEMBLY FOR A SURGICAL INSTRUMENT

CROSS REFERENCE TO RELATED APPLICATIONS

This is a national entry of International Patent Application No. PCT/IB2021/053861, filed on May 6, 2021, which claims priority to and all the benefits of U.S. Provisional Patent Application No. 63/021,141, filed on May 7, 2020, the entire contents of each being hereby incorporated by reference.

BACKGROUND

1. Field of the Disclosure

The present disclosure generally relates to a cutting assembly and a drive assembly for a surgical instrument.

2. Description of the Related Art

It is known that medical practitioners have found it useful to use surgical instruments to assist in the performance of surgical procedures. The practitioner is able to position the surgical instrument at a site on a patient at which the surgical instrument is to perform a medical or surgical procedure. Many surgical instruments have been developed for use in surgical procedures, in particular, endoscopic procedures, to reduce incision size and improve access and visibility, thereby enhancing surgical outcomes with quicker recovery. Some surgical instruments include a cutting assembly removably coupled to a drive assembly. Typical cutting assemblies may include two tubes, one within another, or a single tube defining a cutting window. Alternatively, some cutting assemblies include a single tube within which and a shaft having a bur is rotatably disposed. Such cutting devices may be an ear, nose, and throat (ENT) shaver or bur device.

Removably coupling the cutting assembly to the drive assembly of the surgical instrument typically occurs immediately prior to the performance of the surgical procedure. With cutting assemblies that include two tubes, the inner tube is rotatable within an outer tube. The inner and outer tubes may be arranged such that an irrigating fluid may be directed in a space defined between the inner and outer tubes. Consequently, the inner and outer tubes in typical cutting assemblies may not be rigidly coupled to one another, and the inner tube may undesirably move or shift during handling of the cutting assembly, particularly after removal from packaging and prior to coupling the cutting assembly with the drive assembly.

Moreover, the drive assemblies known in the art often include suction and irrigation ports. These suction and irrigation ports are configured to be coupled to suction and irrigation tubes, respectively. However, the placement of the suction and irrigation ports in typical drive assemblies often result in the suction and irrigation tubes interfering with one another during the performance of the surgical procedure. Furthermore, the placement of the suction and irrigation ports in typical drive assemblies may not provide adequate clearance for the practitioner's hand for ease with coupling the suction and irrigation tubes to the suction and irrigation ports, respectively.

As such, there remains a need to provide for an improved surgical instrument that overcomes one or more of the aforementioned disadvantages.

SUMMARY

The present disclosure is directed to a cutting assembly and a drive assembly for a surgical instrument. The cutting assembly is configured to be removably coupled to the drive assembly. The cutting assembly includes an outer tube extending along an axis, and a cutting implement. The cutting implement includes a distal cutting end and a cutting shaft coupled to the distal cutting end. The cutting shaft extends along the axis and is coaxially disposed within and rotatable relative to the outer tube. The cutting assembly also includes a drive hub defining a bore. The cutting assembly further includes a seal disposed about the drive hub. The cutting shaft may be an inner tube defining a lumen and rotatably disposed within the outer tube such that the distal cutting end is a cutting window. The lumen may be in fluid communication with the cutting window. Optionally, the cutting shaft is solid, and the distal cutting end is a bur. The cutting shaft may even be the inner tube defining the lumen, and the distal cutting end may be a bur. The outer tube may define a distal tube opening through which the cutting shaft and/or bur extends.

The cutting assembly includes an outer hub. The outer hub may include a proximal portion defining a cavity. The outer hub further defines an irrigation aperture in fluid communication with the cavity defined by the proximal portion of the outer hub. The cutting shaft of the cutting implement extends through the irrigation aperture into the cavity. The outer tube is rigidly coupled to the outer hub. The cutting shaft extends along the axis through the outer tube and the outer hub such that a proximal end of the cutting shaft is disposed within the cavity. The proximal end of the cutting shaft may be disposed within the bore and may be rigidly coupled to the drive hub. The seal may be coupled to the outer hub and may be at least partially disposed within the cavity. The cutting implement and the drive hub may be slidably moveable relative to the outer hub between a first position in which the retention flange is distal to the seal and fluid is permitted to flow through the cavity to the irrigation aperture, and a second position in which the retention flange contacts the seal. In the first position, the retention flange may be positioned between the distal end of the seal and the proximal portion of the outer hub. The retention flange may be positioned at, or optionally adjacent to, the distal end of the seal. The retention flange may be positioned at, or optionally adjacent to, the distal end of the seal when the drive hub is moved from the first position toward the second position.

In certain implementations, the outer hub may be disposed at least partially about the outer tube, the cutting shaft, and the drive hub. The outer hub may be engageable by a latching mechanism to removably couple the cutting assembly to the drive assembly. The proximal portion may have an expanded diameter portion which at least partially defines the cavity. The expanded diameter portion of the proximal portion of the outer hub has a greater internal diameter as compared to other sections of the proximal portion of the outer hub. The expanded diameter portion may be at a proximal end of the proximal portion. The expanded diameter portion may be shaped as to form a step or a series of steps into the outer hub. Optionally, the expanded diameter portion may be spaced from the proximal end of the proximal portion. The expanded diameter portion may be shaped as to define a groove into the outer hub. The seal may include a locking tab engageable with the expanded diameter portion of the proximal portion of the outer hub. The locking tab of the seal may extend radially away from the axis relative to a body of the seal.

In certain implementations, the drive hub includes a retention flange extending radially away from the axis. The retention flange may be spaced from the seal such that the retention flange is disposed axially between the seal and the outer tube. The drive hub and the cutting implement may be movably slidable relative to the outer hub when the cutting assembly is not detachably coupled with the drive assembly of the surgical instrument. The drive assembly may have a handpiece defining a handpiece irrigation path. The cutting assembly may include the outer hub including the proximal portion defining the cavity. The cutting assembly may include the outer tube extending along the axis and rigidly coupled to the outer hub. The cutting shaft may extend along the axis through the outer tube and the outer hub such that the proximal end of the cutting shaft is disposed within the cavity. The proximal end of the cutting shaft may be disposed within the bore of the drive hub and may be rigidly coupled to the drive hub. The seal may be coupled to the outer hub. The seal may be at least partially disposed within the cavity.

In certain implementations, the retention flange has a first radius relative to the axis. The innermost point of the seal has a second radius relative to the axis. The first radius may be greater than the second radius to prevent the drive hub from moving axially past the seal. The drive hub may have a distal end. The distal end of the drive hub may have a third radius relative to the axis. The third radius of the drive hub at the distal end of the drive hub may be less than the first radius of the retention flange. Optionally, the retention flange may be spaced apart from the distal end of the drive hub. The retention flange may be at the distal end of the drive hub such that the retention flange is the axial terminus of the drive hub. The drive hub may have a proximal end spaced from the distal end of the drive hub. The proximal end of the drive hub may have a radius approximately equal to, or optionally exactly equal to, the third radius of the distal end of the drive hub. The retention flange and the drive hub may be in physical contact with one another such that the retention flange abuts the seal in the second position.

In certain implementations, the retention flange includes a first retention surface facing the seal, and a second retention surface facing the retention flange. The first retention surface of the retention flange may abut the second retention surface of the seal in the second position. The first retention surface of the retention flange may be spaced apart from the second retention surface of the seal when moved from the second position toward the first position. The retention flange may extend completely circumferentially about the axis to form a general disk shape. Optionally, the retention flange may extend only partially about the axis. The retention flange may extend radially away from the axis at two or more points circumferentially spaced from one another about the axis. Optionally, the retention flange may form a generally polygonal shape, such as, but not limited to, triangular, rectangular, pentagonal, hexagonal, heptagonal, or octagonal.

In certain implementations, the seal may be annular in shape between proximal and distal ends of the seal to define an irrigation channel. The retention flange may be positioned between the distal end of the seal and the proximal portion of the outer hub when the drive hub, and thus the cutting assembly, is removably coupled with the drive assembly of the surgical instrument so as to provide the irrigation channel between the seal and the drive hub. The outer hub may also define seating holes into which the seal may at least partially extend. The seal may deform to at least partially be seated within the seating holes defined by the outer hub. The seal may have a lip that extends at least partially into the seating holes to prevent rotation of the seal relative to the outer hub. The seal may have an innermost point relative to the drive hub. The retention flange may be disposed axially between the innermost point of the seal and the outer tube.

In certain implementations, the innermost point of the seal may be radially aligned with the locking tab of the seal. The innermost point of the seal may be radially spaced from the locking tab of the seal such that the innermost point of the seal is disposed radially between the locking tab of the seal and the axis. The innermost point of the seal may be radially aligned with the expanded diameter portion of the outer hub. The retention flange may be capable . . . of being unobstructed by the seal radially between the drive hub and the outer hub. The retention flange may be moveable between a first flange position and a second flange position. In the first flange position, the retention flange is unobstructed by the seal radially between the retention flange and the outer hub. In the second flange position, the retention flange is obstructed by the seal radially between the retention flange and the outer hub such that the seal is disposed between the retention flange and the outer hub.

The cutting assembly may further include an irrigation spacer disposed distal to the drive hub. The irrigation spacer may include an inner irrigation spacer surface facing the axis. The inner irrigation spacer surface may extend at least partially circumferentially about the axis at a first radial distance. The inner irrigation spacer surface may define a bore through which the outer tube is disposed. Moreover, the irrigation spacer may include an outer irrigation spacer surface facing away from the axis. The outer irrigation spacer surface may extend at least partially circumferentially about the axis at a second radial distance. It is to be appreciated that the second radial distance may be greater than the first radial distance. The outer irrigation spacer surface may be spaced from the inner irrigation spacer surface such that the inner irrigation spacer surface is disposed radially between the axis and the outer irrigation spacer surface. The irrigation spacer may define an irrigation passageway between the first and second radial distances. The irrigation spacer may comprise plastic, including injection-molded plastic. Optionally, the irrigation spacer may comprise a variety of materials, including, but not limited to, metals including stainless steel, ceramics, and composite materials.

In certain implementations, the irrigation spacer may have fins extending radially away from the axis. The fins may be spaced circumferentially about the axis. The fins may define the irrigation passageway. The irrigation spacer may have two, three, four, five, six, seven, eight, or more than eight fins. The outer irrigation spacer surface may be interrupted and thus does not extend completely circumferentially about the axis. Optionally, the irrigation passageway may be defined by the irrigation spacer without any fins. The irrigation spacer may be completely solid but for the bore defined by the inner irrigation spacer surface and but for the irrigation passageway defined between the inner and outer irrigation spacer surfaces. The outer irrigation spacer surface may extend completely circumferentially about the axis at the second radial distance without interruption. The outer hub may have a key that extends at least partially into the irrigation passageway to limit rotation of the irrigation spacer relative to the outer hub. The irrigation spacer may be engageable with the drive hub. The cutting assembly may further include at least one washer disposed between the irrigation spacer and the drive hub to assist the irrigation spacer in engaging the drive hub. The at least one washer may be one washer, two washers, three washers, or more than three washers.

In certain implementations, the outer hub may be disposed in the cavity defined by the proximal portion of the outer hub. The outer hub may have an inner hub surface that tapers distally toward the axis. The inner hub surface may have a smaller diameter at the distal end of the inner hub surface and may have a larger diameter at the proximal end of the inner hub surface. The outer irrigation spacer surface of the irrigation spacer may taper distally toward the axis. Said differently, the outer irrigation spacer surface may have a smaller diameter at the distal end of the outer irrigation spacer surface and may have a larger diameter at the proximal end of the outer irrigation spacer surface. The inner hub surface and the outer irrigation spacer surface may be engageable with one another to maintain a relative axial position between the outer hub and the irrigation spacer. Optionally, the inner hub surface and the outer irrigation spacer surface may be press-fit with one another. Optionally, the tapered profiles of the inner hub surface and the outer irrigation spacer surface may only loosely fit together.

The drive assembly for the surgical instrument includes the handpiece extending along the axis. The handpiece may include a distal end defining a distal opening inwardly from the distal end that is dimensioned to receive the outer hub of the cutting assembly. The handpiece may also include a proximal end defining a proximal opening inwardly from the proximal end. A back cap may be coupled to the handpiece so as to be at least partially disposed within the proximal opening. A motor may be disposed within the handpiece. The motor may have an output shaft rotatable about the axis. A coupling member may be attached to the output shaft. Optionally, the handpiece may include the latching mechanism coupled to the distal end of the handle body. The latching mechanism may include a button aligned radially with the upper aspect of the handpiece in the operative orientation.

In certain implementations, the drive assembly may also include an irrigation port coupled to the handpiece. The drive assembly may further include a suction port coupled to the back cap. A proximal end of the irrigation port may be positioned distal to a position where the suction port is coupled to the back cap. The irrigation port may include a distal end coupled to the handpiece and the proximal end opposite the distal end. The suction port may include a distal portion disposed within and coupled to the handpiece. Optionally, the distal portion of the suction port may be disposed within and coupled to the back cap of the handpiece. The suction port may also include a proximal portion extending proximally from the handpiece. The proximal portion of the suction port may extend proximally from the back cap of the handpiece. The proximal end of the irrigation port may be positioned axially distal to the proximal portion of the suction port. The proximal end of the irrigation port may be axially distal to the proximal portion of the suction port. The proximal portion of the irrigation port may begin where the irrigation port extends from the back cap. The proximal portion of the suction port may be axially distal to where the irrigation port extends from the back cap. The irrigation port and the suction port may have a barb configuration.

In certain implementations, the drive assembly may further include an electrical connector coupled to the handpiece. The electrical connector may be disposed in, or optionally directly attached to, the back cap of the handpiece. The electrical connector may be screwed into the back cap of the handpiece to secure the electrical connector to the drive assembly. Optionally, the electrical connector may be press-fit to, welded to, or otherwise mechanically affixed to the back cap of the handpiece. Optionally, the motor of the surgical instrument may be powered by a battery disposed within the surgical instrument. A proximal end of the electrical connector may be spaced from the proximal end of the suction port such that the suction port is disposed axially between the electrical connector and the irrigation port. In order from a proximal end of the surgical instrument to a distal end of the surgical instrument, the irrigation port, the suction port, and the electrical connector may be spaced from one another along the axis, respectively. The back cap may at least partially define an electrical channel through which electrical power may travel to power the motor. Optionally, the back cap may completely define the electrical channel. Optionally, the handpiece may at least partially define the electrical channel through which the electrical power may travel to power the motor.

In certain implementations, the back cap may have a suction portion adjacent to the suction port and an electrical portion adjacent to the electrical connector. The suction portion may be spaced from the proximal end of the irrigation port such that the suction portion is disposed axially between the electrical portion and the proximal end of the irrigation port. The irrigation port, therefore, may be axially distal relative to the back cap. The suction port may be generally aligned with the axis and disposed at a general radial center relative to the handpiece. The suction port, the suction flow path, the drive hub, and the lumen of the inner tube may lie in a general line parallel to the axis through the general radial center relative to the handpiece.

In certain implementations, the handle body may also include a saddle region near the proximal end of the handpiece. The saddle region may define a first recess and may define a lower aspect of the handpiece in an operative orientation. The lower aspect may further include a curved surface between the saddle region and the distal end of the handle body. The handle body may define a second recess near the distal end of the handle body and extending annularly about the longitudinal axis. The handle body may further include an apex region extending longitudinally between the second recess and the proximal end. The apex region may extend on either side of the surgical instrument. The apex region may include opposing surfaces that are relatively flatter than the curved surface of the lower aspect. The opposing surfaces are on either side of the surgical instrument. The opposing surfaces may be angling towards and meeting one another to define an upper aspect of the handpiece in the operative orientation. Optionally, the handle body may further define a third recess extending longitudinally along at least a portion of the opposing surfaces. The apex region may define the handpiece irrigation path internal to the handle body. The handpiece may further include the irrigation port coupled to the apex region and in fluid communication with the handpiece irrigation path. The apex region may be pyramidal in axial section or may be of a variety of shapes in axial section including, but not limited to, oval and rectangular.

BRIEF DESCRIPTION OF THE DRAWINGS

Other advantages of the present disclosure will be readily appreciated, as the same becomes better understood by reference to the following detailed description when considered in connection with the accompanying drawings wherein.

DETAILED DESCRIPTION

Figure 1A:
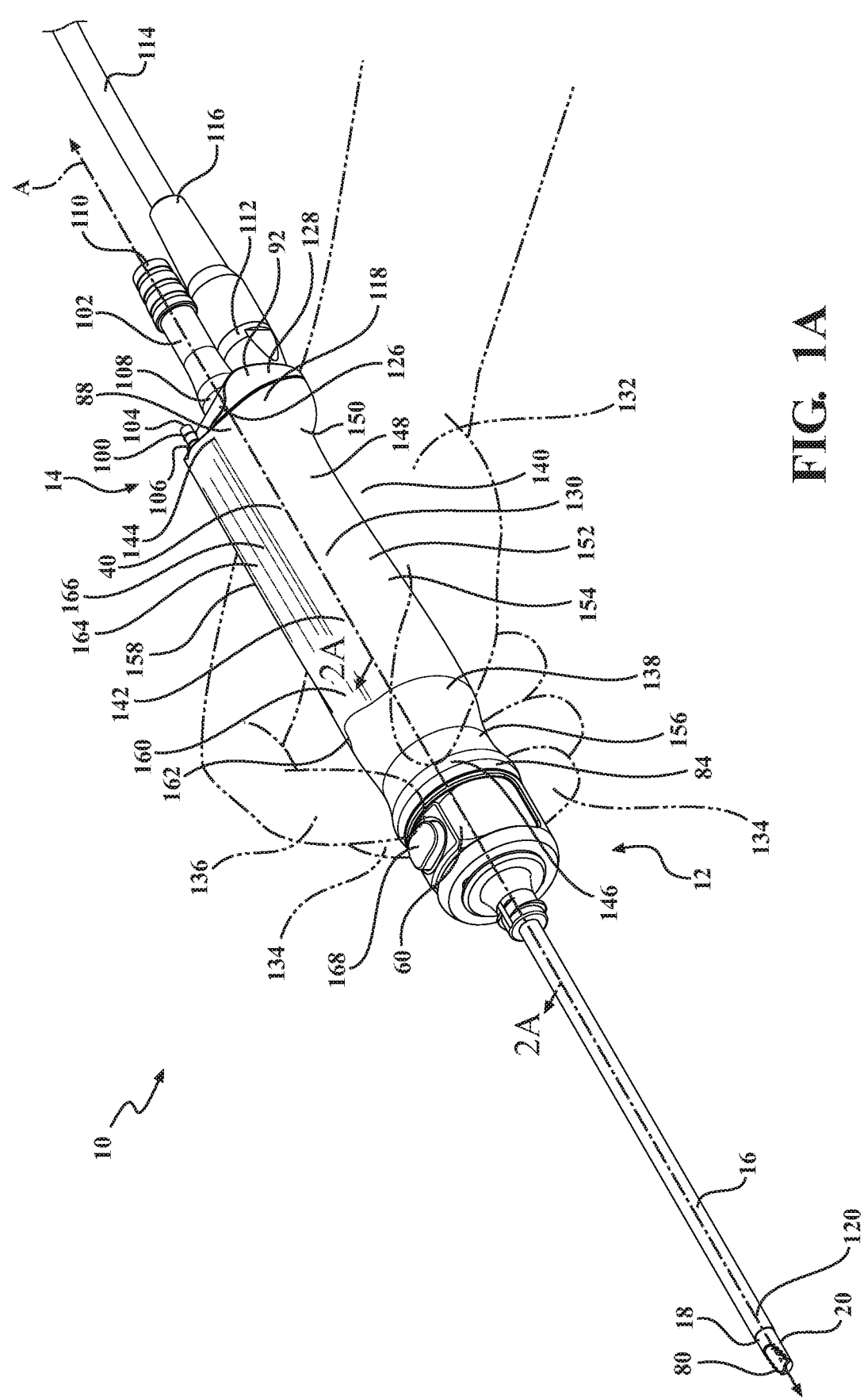
FIG. 1A is a perspective view of a surgical instrument having a cutting assembly, a drive assembly, and a cutting implement including a cutting window.
Figure 1B:
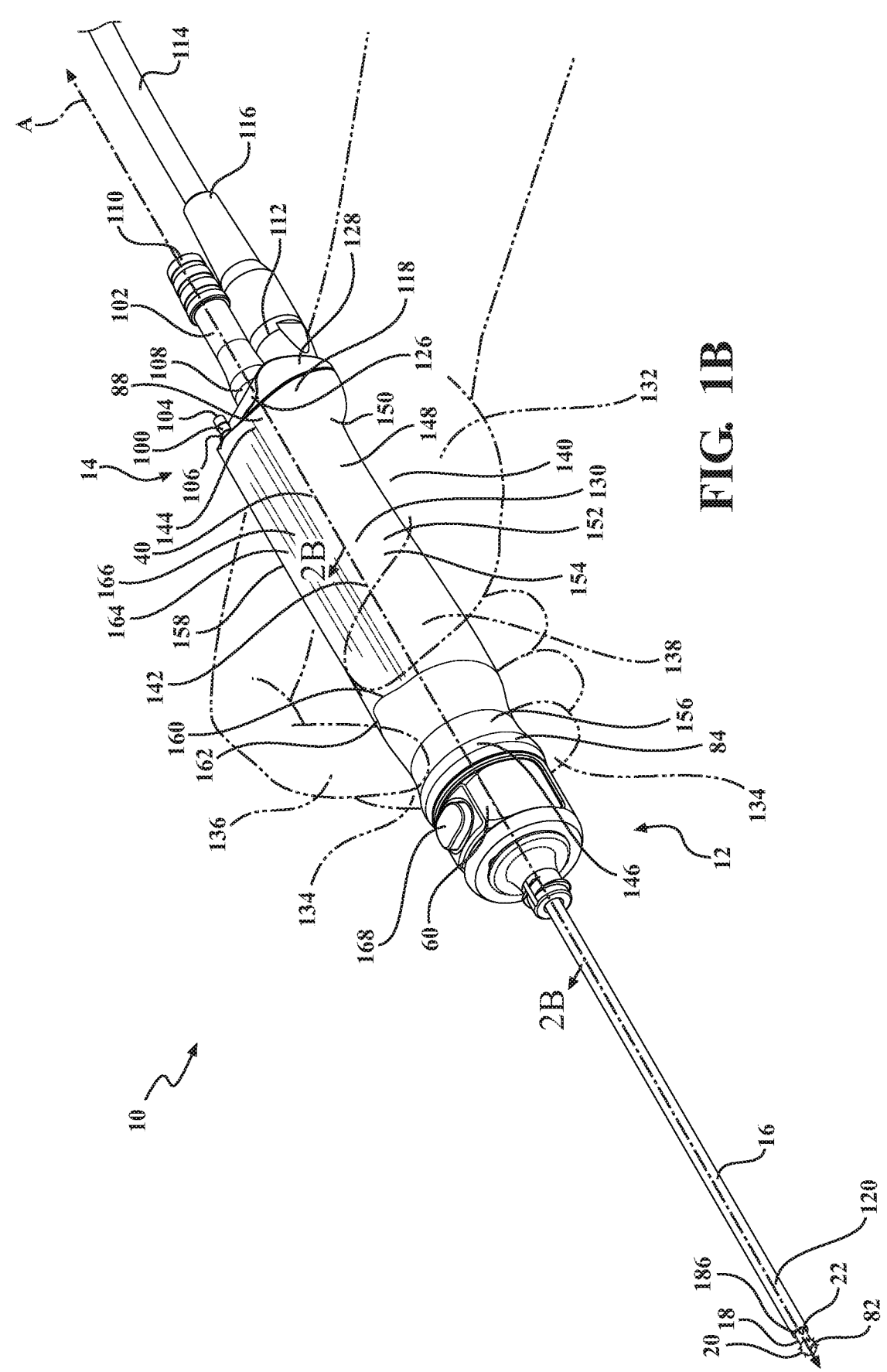
FIG. 1B is a perspective view of a surgical instrument having a cutting assembly, a drive assembly, and a cutting implement including a bur.

With reference to the Figures, wherein like numerals indicate like parts throughout the several views, a surgical instrument 10 is shown in perspective views in FIGS. 1A and 1B. The surgical instrument 10 includes a cutting assembly 12 and a drive assembly 14. The surgical instrument 10 may be for use in a medical procedure for a patient (not shown). In one implementation, the cutting assembly 12 is a shaver that is disposable and used for resecting tissue during endoscopic sinus surgery. The drive assembly 14 is used to rotate a portion of the cutting assembly 12 to remove tissue, bone, etc. from a surgical site of the patient.

The cutting assembly 12 includes an outer tube 16 extending along an axis A, and a cutting implement 18. The cutting implement 18 includes a distal cutting end 20 and a cutting shaft 22 coupled to the distal cutting end 20, extending along the axis A, and coaxially disposed within and rotatable relative to the outer tube 16 with the drive assembly 14. The cutting assembly 12 also includes a drive hub 24 defining a bore 26 adapted to slidably receive a proximal end 28 of the cutting shaft 22. The cutting assembly 12 further includes a seal 30 coupled to an outer hub 34. At least a portion of the seal 30 may be disposed about the drive hub 24.

The drive hub 24 includes a retention flange 32. Although not required, the drive hub 24 and the retention flange 32 may be integral, unitary, and formed as one-piece. The retention flange 23 may extend radially away from the axis A, spaced from the seal 30 such that the retention flange 32 is disposed axially between the seal 30 and the outer tube 16, and configured to prevent the drive hub 24 from moving axially past the seal 30 to retain the cutting shaft 22 within the outer tube 16. By preventing the drive hub 24 from moving axially past the seal 30 to retain the cutting shaft 22 within the outer tube 16, the retention flange 32 maintains the drive hub 24 as ready for engagement with the drive assembly 14. In particular, the arrangement limits the proximal movement of the drive hub 24 during handling of the cutting assembly 12 after removal from packaging in the sterile field and prior to coupling the drive hub 24 with the drive assembly 14. If, by contrast, the drive hub 24 were not maintained as ready for engagement, the cutting implement 18 may be ejected with improper handling, which would render the cutting assembly 12 either inoperable for use or unsterile for use. The improved seal 30 of the present disclosure advantageously addresses this shortcoming by permitting the user to handle the cutting assembly 12 without concern for such an occurrence while providing an improved irrigation path through the cutting assembly 12.

In one implementation, the cutting assembly 12 includes the outer hub 34 comprising a proximal portion 36 defining a cavity 38. The outer tube 16 extends from the outer hub 34, and the outer tube 16 may be rigidly coupled to the outer hub 34. The cutting shaft 22 may extend along the axis A through the outer tube 16 and the outer hub 34 such that a proximal end 28 of the cutting shaft 22 is disposed within the cavity 38. Additionally, the proximal end 28 of the cutting shaft 22 may be disposed within the bore 26 of the drive hub 24 and may be rigidly coupled to the drive hub 24. The seal 30 may be coupled to the outer hub 34 and may be at least partially disposed within the cavity 38. The cutting implement 18 and the drive hub 24 may be slidably moveable relative to the outer hub 34 between a first position in which the retention flange 32 is between the seal 30 and the proximal portion 36 of the outer hub 34 (see FIGS. 2A and 3A), and a second position in which the retention flange 32 contacts the seal 30 (see FIGS. 2B and 3B).

The drive hub 24 and the cutting implement 18 are movably slidable relative to the outer hub 34 when the cutting assembly 12 is not detachably coupled with the drive assembly 14 of the surgical instrument 10. Further, the drive hub 24 and the cutting implement 18 may be freely removable from the outer hub 34 and the outer tube 16, respectively, when the cutting assembly 12 is not detachably coupled with the drive assembly 14 of the surgical instrument 10. The second position of the drive hub 24 and the cutting implement 18 limits the extent to the drive hub 24 may slidably move proximally within the outer hub 34. More specifically, because the retention flange 32 contacts the seal 30 in the second position, the contact between the retention flange 32 and the seal 30 prevents the drive hub 24 from moving axially past the seal 30.

In one implementation, an irrigation flow path 192 is defined between the outer tube 16 and the cutting shaft 22. In this implementation, the retention flange 32 of the drive hub 24 is configured to be spaced apart from the distal end 46 of the seal 30, and the drive hub 24 is configured to be removably coupled to the drive assembly 14 of the surgical instrument 10 to permit fluid to flow from the handpiece irrigation path 42 to the irrigation flow path 192. In other words, the spacing of the retention flange 32 relative to the seal 30 permits irrigating fluid to flow from the handpiece irrigation path 42, past the seal 30 and the drive hub 24, to the irrigation flow path 192 without interruption to adequately provide irrigating fluid to the surgical site of the patient.

The drive assembly 14 may have a handpiece 40 defining a handpiece irrigation path 42. In such an arrangement, the cutting assembly 12 includes the outer hub 34 including the proximal portion 36 defining the cavity 38, and includes the outer tube 16 extending along the axis A and rigidly coupled to the outer hub 34. The cutting shaft 22 may extend along the axis A through the outer tube 16 and the outer hub 34 such that the proximal end 28 of the cutting shaft 22 is disposed within the cavity 38. Additionally, the proximal end 28 of the cutting shaft 22 may be disposed within the bore 26 of the drive hub 24 and may be rigidly coupled to the drive hub 24. The seal 30 may be coupled to the outer hub 34 and may be at least partially disposed within the cavity 38.

Figure 2A:
FIG. 2A is a cross-sectional view of a portion of the surgical instrument taken along line 2A-2A of FIG. 1A. A retention flange of a drive hub is shown as being positioned distal to a seal.
Figure 2B:
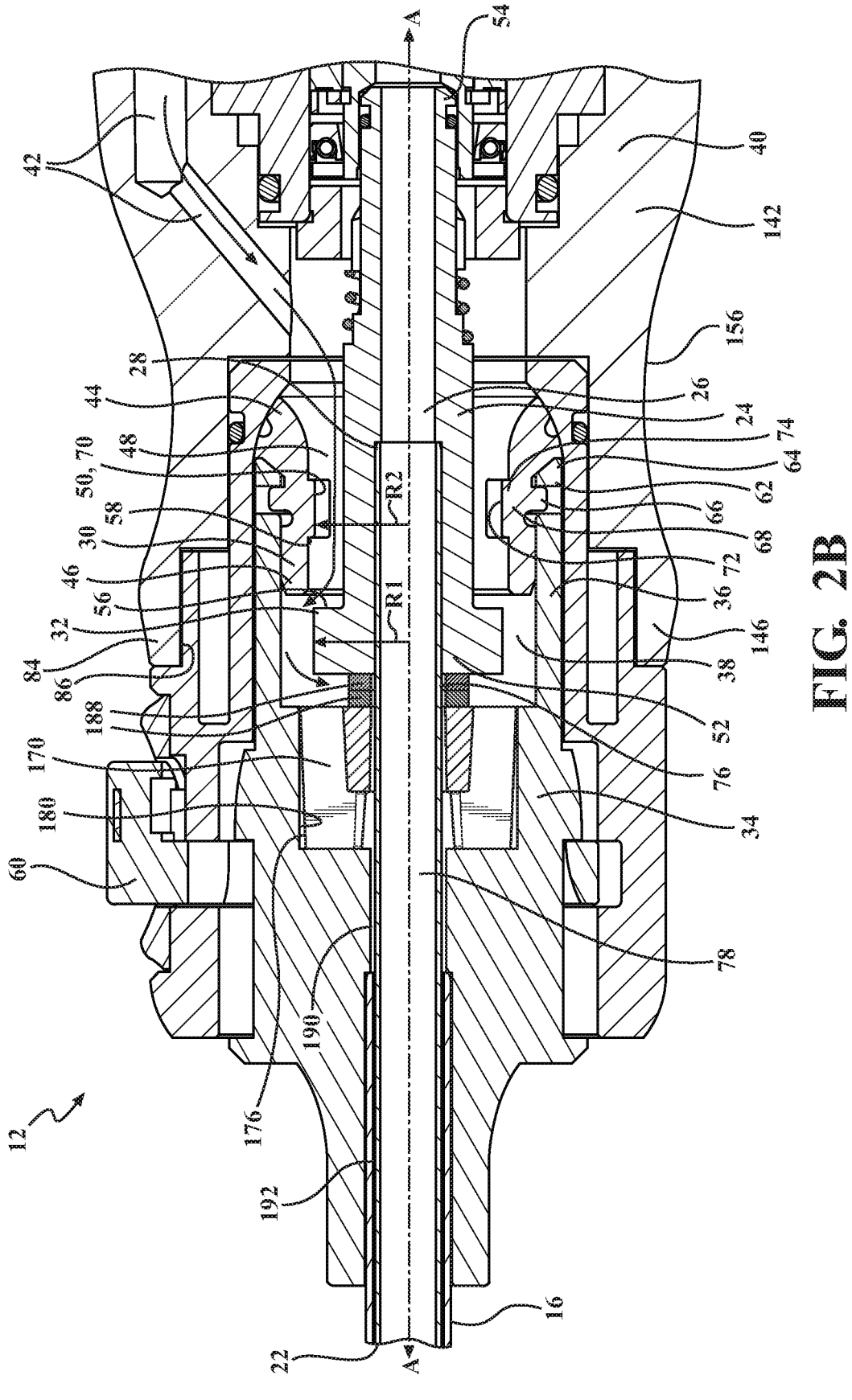
FIG. 2B is a cross-sectional view of the surgical instrument taken along line 2B-2B of FIG. 1B. An irrigation spacer defines a bore through which the cutting shaft extends, and provides a stop for distal axial movement of the drive hub.

The seal 30 may be annular in shape between proximal and distal ends 44, 46 of the seal 30 to define an irrigation channel 48 configured to be in fluid communication with the handpiece irrigation path 42 defined by the handpiece 40 of the drive assembly 14 of the surgical instrument 10. In this implementation, the retention flange 32 is configured to be spaced apart from the distal end 46 of the seal 30, and the retention flange 32 may be positioned between the distal end 46 of the seal 30 and the proximal portion 36 of the outer hub 34 when the cutting assembly 12, is removably coupled with the drive assembly 14. The arrangement provides the irrigation channel 48 between the seal 30 and the drive hub 24, as represented in FIGS. 2A and 2B. The irrigation channel 48 defined between the seal 30 and the drive hub 24 results in increased flowrates of, and better control of, the flow of irrigating fluid from the handpiece irrigation path 42 defined by the handpiece 40, through the irrigation channel 48 defined between the seal 30 and the drive hub 24, and to the surgical site on the patient.

The seal 30 may have an innermost point 50 relative to the drive hub 24. The retention flange 32 may be disposed axially between the innermost point 50 of the seal 30 and the outer tube 16. The retention flange 32 may be unable to move axially past the innermost point 50 of the seal 30. As a result, the drive hub 24 is maintained as ready for engagement with the drive assembly 14. The retention flange 32 has a first radius R1 relative to the axis A. The innermost point 50 of the seal 30 has a second radius R2 relative to the axis A. The first radius R1 may be greater than the second radius R2 to prevent the drive hub 24 from moving axially past the seal 30. The drive hub 24 may have a distal end 52. In other implementations, the distal end 52 of the drive hub 24 may have a third radius relative to the axis A. The third radius of the drive hub 24 at the distal end 52 of the drive hub 24 may be less than the first radius R1 of the retention flange 32. Because the distal end 52 of the drive hub 24 may have the third radius that is less than the first radius R1 of the retention flange 32, the retention flange 32 may be spaced apart from the distal end 52 of the drive hub 24. It is to be appreciated, however, that the retention flange 32 may be at the distal end 52 of the drive hub 24 such that the retention flange 32 is the axial terminus of the drive hub 24. The third radius of the distal end 52 of the drive hub 24 may be less than the second radius R2 of the innermost point 50 of the seal 30 to allow the distal end 52 of the drive hub 24 to easily move axially past the seal 30. It is to be appreciated that the drive hub 24 may have a proximal end 54 spaced from the distal end 52 of the drive hub 24. The proximal end 54 of the drive hub 24 may have a radius approximately equal to, or exactly equal to, the third radius of the distal end 52 of the drive hub 24. In this implementation, both the proximal and distal ends 52, 54 of the drive hub 24 are sized to be able to move axially past the seal 30.

Figure 3A:
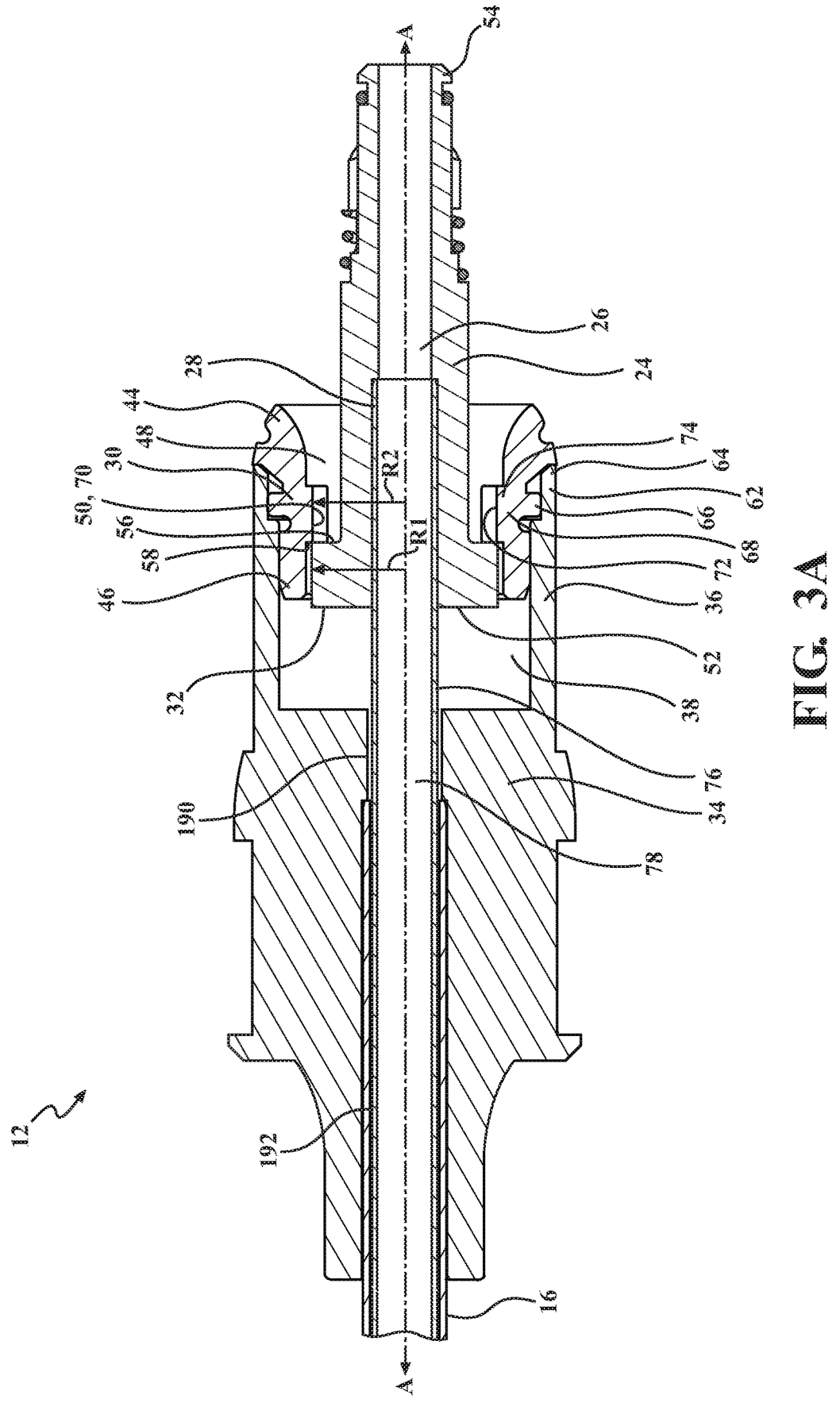
FIG. 3A is a cross-sectional view of a portion of the cutting assembly of FIG. 2A with the retention flanges contacting the seal to limit proximal movement of the drive hub and cutting shaft relative to the outer hub.
Figure 3B:
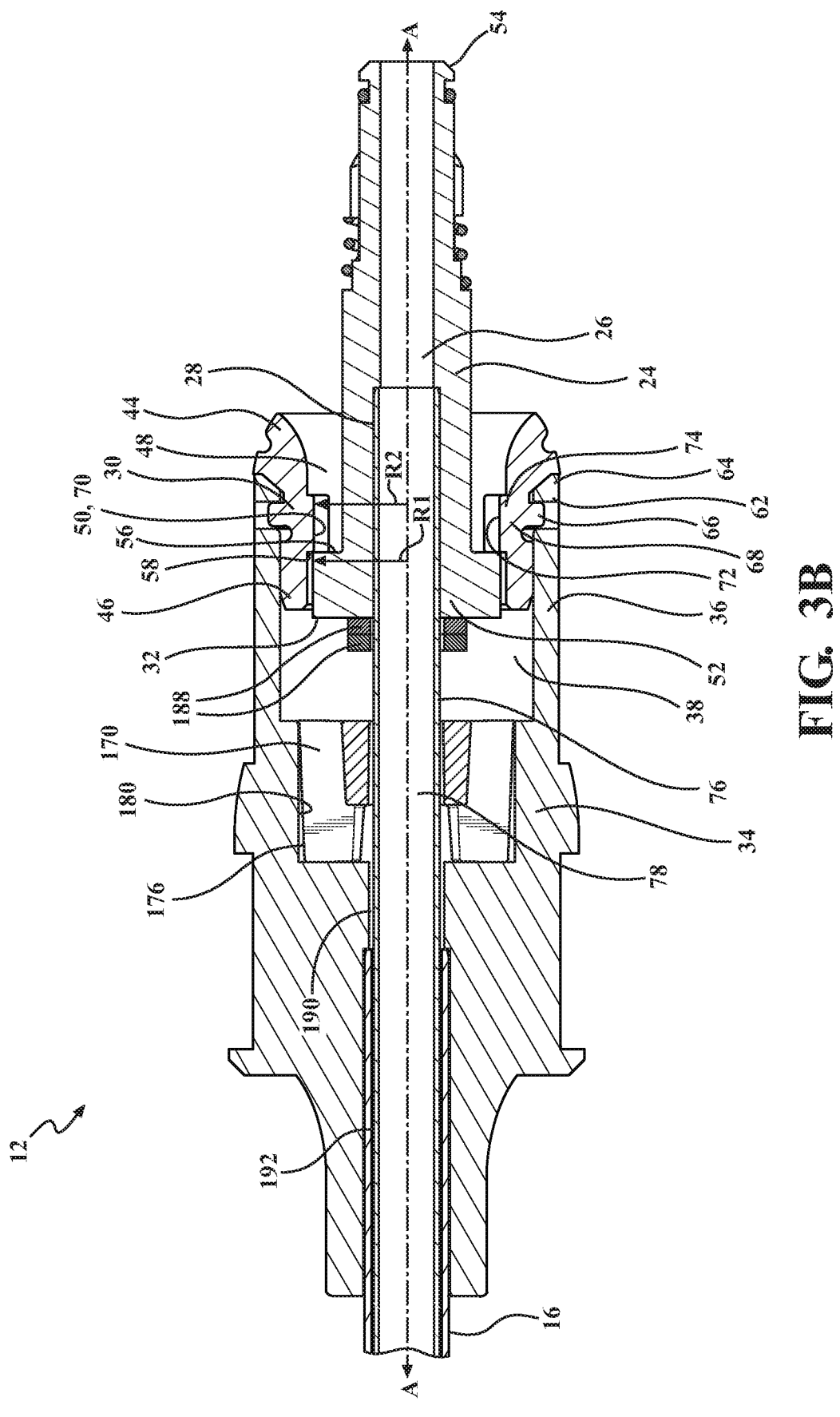
FIG. 3B is a cross-sectional view of a portion of the cutting assembly of FIG. 2B with the retention flanges contacting the seal to limit proximal movement of the drive hub and cutting shaft relative to the outer hub.

The retention flange 32 and the seal 30 may be configured to be in an abutting relationship with one another to prevent the drive hub 24 from moving axially past the seal 30, either directly or through intermediate structures. In particular, with the cutting assembly 12 not coupled to the drive assembly 14, the retention flange 32 may abut the seal 30 in the second position, as shown in FIGS. 3A and 3B. With the cutting assembly 12 removably coupled to the drive assembly 14, the retention flange 32 may be spaced from the seal 30 in the first position, as shown in FIGS. 2A and 2B.

The retention flange 32 may include a first retention surface 56 facing the seal 30, and the seal 30 may include a second retention surface 58 facing the retention flange 32. The first and second retention surfaces 56, 58 may be configured to prevent the drive hub 24 from moving axially past the seal 30. With the cutting assembly 12 is not removably coupled to the drive assembly 14 in the surgical instrument 10, the first retention surface 56 of the retention flange 32 may abut the second retention surface 58 of the seal 30 in the second position. With the cutting assembly 12 removably coupled to the drive assembly 14 in the surgical instrument 10, the drive hub 24 moves to the first position and the first retention surface 56 and the second retention surface 58 may be spaced apart from one another.

The outer hub 34 may be disposed at least partially about the outer tube 16, the cutting shaft 22, and the drive hub 24 to assist in removably coupling the cutting assembly 12 to the drive assembly 14. The outer hub 34, in a non-limiting example, may be engageable by a latching mechanism 60 to removably couple the cutting assembly 12 to the drive assembly 14. In the implementations where the outer hub 34 has the proximal portion 36 defining the cavity 38 into which the drive hub 24 is received, the proximal portion 36 may have an expanded diameter portion 62 which at least partially defines the cavity 38. The expanded diameter portion 62 of the proximal portion 36 of the outer hub 34 has a greater diameter as compared to other sections of the proximal portion 36 of the outer hub 34. The expanded diameter portion 62 may be at a proximal end 64 of the proximal portion 36. The expanded diameter portion 62 may be shaped as to form a step or a series of steps into the outer hub 34. Alternatively, the expanded diameter portion 62 may be spaced from the proximal end 64 of the proximal portion 36. In one example, the expanded diameter portion 62 may be shaped as to define a groove into the outer hub 34.

The seal 30 also may be compressed when disposed within the cavity 38 defined by the proximal portion 36 of the outer hub 34. The outer hub 34 may also define seating holes into which the seal 30 may at least partially extend. Although not required, the seal 30 may deform to at least partially be situated within the seating holes. The seating holes may prevent rotation of the seal 30 relative to the outer hub 34. More specifically, the seal 30 may have a lip that extends at least partially into the seating holes to prevent rotation of the seal 30 relative to the outer hub 34. The seal 30 may include a locking tab 66 engageable with the expanded diameter portion 62 of the proximal portion 36 of the outer hub 34. The locking tab 66 of the seal 30 may extend radially away from the axis A relative to a body 68 of the seal 30. The locking tab 66 also may be sized and configured to fit within the step or series of steps formed by the expanded diameter portion 62, or may be sized and configured to fit within the groove defined by the expanded diameter portion 62 into the outer hub 34.

The retention flange 32 may be capable of being unobstructed by the seal 30 radially between the drive hub 24 and the outer hub 34. The retention flange 32 may be moveable between a first flange position and a second flange position. In the first flange position, as shown in FIG. 2A, the retention flange 32 is unobstructed by the seal 30 radially between the retention flange 32 and the outer hub 34. In the second flange position, as shown in FIG. 2B, the retention flange 32 is obstructed by the seal 30 radially between the retention flange 32 and the outer hub 34 such that the seal 30 is disposed between the retention flange 32 and the outer hub 34.

The retention flange 32 may extend completely circumferentially about the axis A to form a general disk shape. However, it is to be appreciated that the retention flange 32 may extend only partially about the axis A, or may extend radially away from the axis A at two or more points circumferentially spaced from one another about the axis A. It is also to be appreciated that the retention flange 32 may form a generally polygonal shape, such as, but not limited to, triangular, rectangular, pentagonal, hexagonal, heptagonal, or octagonal.

Although not required, the innermost point 50 of the seal 30 may be radially aligned with the locking tab 66 of the seal 30. Said differently, the innermost point 50 of the seal 30 may be radially spaced from the locking tab 66 of the seal 30 such that the innermost point 50 of the seal 30 is disposed radially between the locking tab 66 of the seal 30 and the axis A. As such, the innermost point 50 of the seal 30 may be radially aligned with the expanded diameter portion 62 of the outer hub 34. In one implementation, the innermost point 50 of the seal 30 is further defined as a first innermost point 70, and the seal 30 has a second innermost point 72 relative to the drive hub 24. The second innermost point 72 of the seal 30 may be circumferentially spaced from the first innermost point 70 of the seal 30 about the axis A. In other words, the first and second innermost points 70, 72 of the seal 30 may be interrupted by circumferential sections of the seal 30 that are radially further away from the axis A than the first and second innermost points 70, 72 of the seal 30.

The seal 30 further includes a retaining flange 74 extending radially toward the axis A. The retention flange 32 of the drive hub 24 is configured to contact the retaining flange 74 of the seal 30 in the second position. The retaining flange 74 of the seal 30 assists in preventing the drive hub 24 from moving axially past the seal 30. It is to be appreciated that the first and second innermost points 70, 72 of the seal 30 may be disposed on the retaining flange 74. Said differently, the retaining flange 74 may be the radially closest portion of the seal 30 to the axis A. The retention flange 32 of the drive hub 24 and the retaining flange 74 of the seal 30 may be configured to be in an abutting relationship with one another to prevent the drive hub 24 from moving axially past the seal 30. The retaining flange 74 of the seal 30 may be disposed between the proximal and distal ends 44, 46 of the seal 30. As such, the drive hub 24 may be able to move along the axis A such that a portion of the drive hub 24 is axially past the seal 30. However, it is also to be appreciated that the retention flange 32 of the drive hub 24 is not able to move axially past the seal 30. As such, the retention flange 32 may be radially spaced from the seal 30 such that the seal 30 is disposed radially between the outer hub 34 and the drive hub 24.

The retention flange 32 may be configured to be positioned between the distal end 46 of the seal 30 and the proximal portion 36 of the outer hub 34 when the drive hub 24, and thus the cutting assembly 12, is detachably coupled with the drive assembly 14 of the surgical instrument 10. More specifically, in the first position, the retention flange 32 may be positioned distal to the seal 30. It is to be appreciated that the retention flange 32 need not be spaced completely distally past the seal 30 to be distal to the seal 30. In a non-limiting example, only a portion of the retention flange 32 need be distal to the seal 30 for the retention flange 32 to be considered distal to the seal 30. The retention flange 32 may be between the distal end 46 of the seal 30 and the proximal portion 36 of the outer hub 34 when the drive hub 24, and thus the cutting assembly 12, is detachably coupled with the drive assembly 14 of the surgical instrument 10. The retention flange 32 may be positioned at or adjacent to the distal end 46 of the seal 30 when the drive hub 24, and thus the cutting assembly 12, is detachably coupled with the drive assembly 14 of the surgical instrument 10. The retention flange 32 may be positioned at or adjacent to the distal end 46 of the seal 30 when the drive hub 24 is moved from the first position toward the second position.

The drive hub 24 and the cutting implement 18 may be movably slidable relative to the outer hub 34 when the cutting assembly 12 is not detachably coupled with the drive assembly 14 of the surgical instrument 10. The drive hub 24 and the cutting implement 18 may be rigidly coupled to one another and thus may move in unison. Moreover, the drive hub 24 and the cutting implement 18 may also be movably slidable relative to the outer tube 16 of the cutting assembly 12. As such, the retention flange 32 of the drive hub 24 and the retaining flange 74 of the seal 30 are necessary to prevent the drive hub 24 from moving axially past the seal 30, and thus to maintain the drive hub 24 as ready for engagement with the drive assembly 14.

In certain implementations, the cutting shaft 22 is an inner tube 76 defining a lumen 78 and rotatably disposed within the outer tube 16 such that the distal cutting end 20 is a cutting window 80 adapted to be applied to the surgical site of the patient. In other words, the surgical instrument 10 may be a shaver, particularly a shaver. The lumen 78 may be in fluid communication with the cutting window 80. Alternatively, in another implementation as shown in FIG. 1B, the cutting shaft 22 is solid and the distal cutting end 20 is a bur 82. The bur 82 on a cutting shaft 22 that defines the lumen 78 is also contemplated. The cutting shaft 22, including the inner tube 76, and outer tube 16 may be made of a metal material such as stainless steel or a non-metallic material such as a composite depending on the application. A wall thickness of the cutting shaft 22, including the inner tube 76, and the outer tube 16 is relatively thin such as approximately 0.1 to approximately 0.5 millimeters (mm) to be of a relatively small diameter and also to be lightweight. The diameters of the cutting shaft 22, including the inner tube 76, and the outer tube 16 have a relatively small diameter such as approximately 2.0 mm to approximately 5.0 mm so as to work in a small opening of a nasal cavity or oral cavity of the patient and to prevent the practitioner's view from being obstructed. It is contemplated that the cutting shaft 22, particularly the inner tube 76, and the outer tube 16 may be scaled larger or smaller depending on the application.

Referring now to FIGS. 3A and 3B, the cutting assembly 12 may further include an irrigation spacer 170 disposed distal to the drive hub 24. In implementations where the cutting assembly 12 is a shaver, closed distal end prevents distal movement of the cutting shaft 22 relative to the outer tube 16. Such a constraint may not be present on a bur, and in particular the bur of FIG. 1B where the outer tube 16 defines a distal tube opening 186. FIG. 3B shows the outer hub 34 defining an irrigation aperture 190 in fluid communication with the cavity 38 and an annular gap between the outer tube 16 and the cutting shaft 22 The irrigation aperture 190 may be an annular gap surrounding the cutting shaft 22. The irrigation aperture 190 may be in fluid communication with the irrigation channel 48 defined between the drive hub 24 and the seal 30. The distal end 52 of the drive hub 24, positioned adjacent the irrigation aperture 190 (with distal movement of the cutting shaft 22), may limit or occlude the flow of fluid through the irrigation aperture 190. The irrigation spacer 170 of the present implementation advantageously provides for axial spacing of the drive hub 24 from near the irrigation aperture 190 while also providing irrigation passageways 178 to permit robust fluid flow to the irrigation aperture 190. The irrigation passageways 178 may be in fluid communication with the irrigation channel 48 defined between the drive hub 24 and the seal 30 and the irrigation aperture 190 defined by the irrigation spacer 170. To prevent the drive hub 24 from moving distal to the outer hub 34, an outer diameter of the drive hub 24 is greater than an outer diameter of the irrigation aperture 190.

Figure 6:
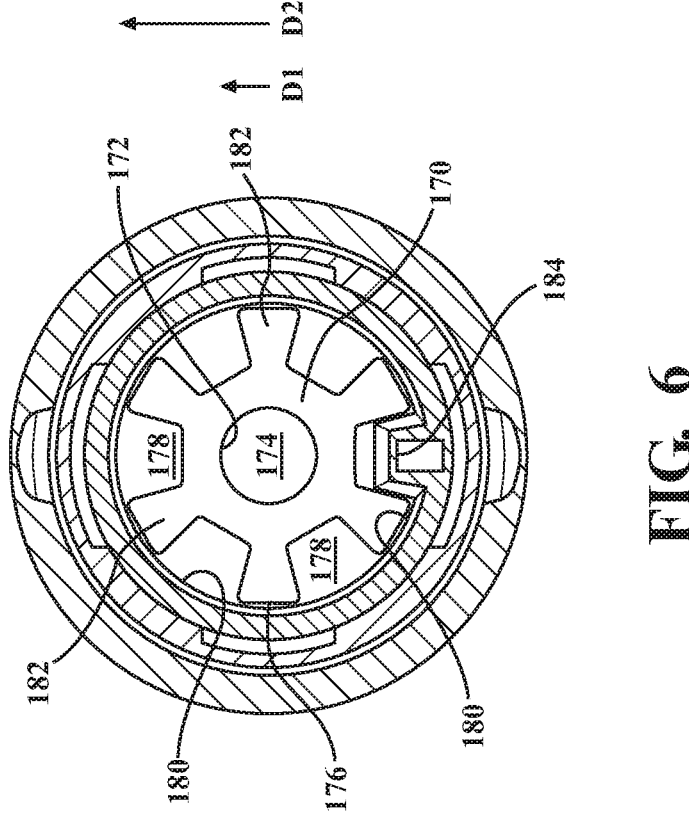
FIG. 6 is a front elevation view of the irrigation spacer positioned within the cutting assembly.
Figure 5:
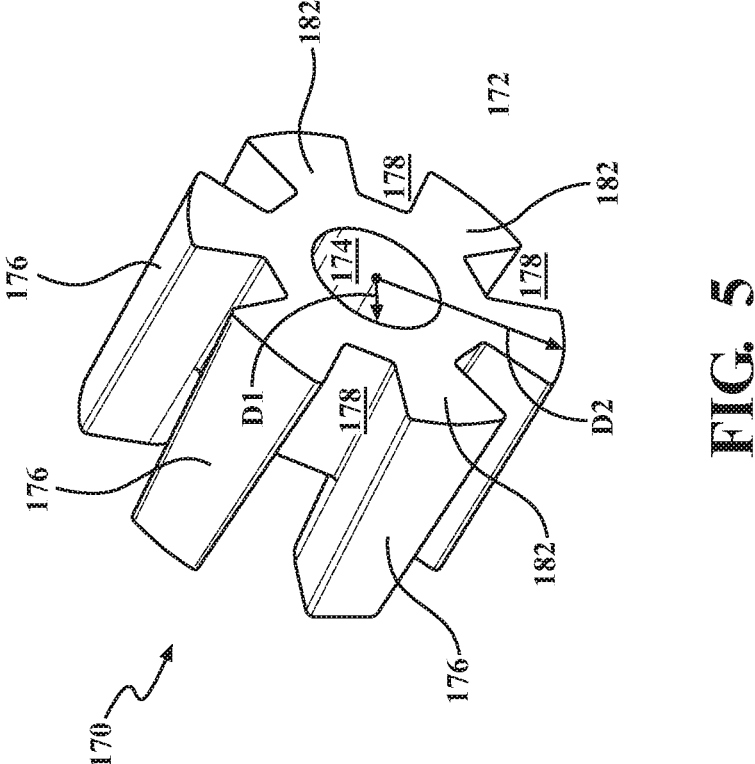
FIG. 5 is a perspective view of an irrigation spacer.

As shown in FIGS. 5 and 6, the irrigation spacer 170 may include an inner irrigation spacer surface 172 facing the axis A. The inner irrigation spacer surface 172 may extend at least partially circumferentially about the axis A at a first radial distance D1. The inner irrigation spacer surface 172 may define a bore 174 through which the outer tube 16 is disposed. Moreover, the irrigation spacer 170 may include an outer irrigation spacer surface 176 facing away from the axis A. The outer irrigation spacer surface 176 may extend at least partially circumferentially about the axis A at a second radial distance D2. It is to be appreciated that the second radial distance D2 is greater than the first radial distance D1. In other words, the outer irrigation spacer surface 176 may be spaced from the inner irrigation spacer surface 172 such that the inner irrigation spacer surface 172 is disposed radially between the axis A and the outer irrigation spacer surface 176.

The irrigation spacer 170 may define the irrigation passageway 178 between the first and second radial distances D1, D2. The irrigation passageway 178 may also be configured to be in fluid communication with the handpiece irrigation path 42 defined by the handpiece 40 of the drive assembly 14. The irrigation passageway 178 allows irrigating fluid to pass through the irrigation spacer 170. More specifically, irrigating fluid may flow from the handpiece irrigation path 42 defined by the handpiece 40 to the distal opening 86 of the handpiece 40, optionally through the irrigation channel 48 defined between the drive hub 24 and the seal 30 if present in the implementation, through the irrigation passageway 178 defined by the irrigation spacer 170 if present in the implementation, through the irrigation aperture 190 defined by the outer hub 34, through the irrigation flow path 192 defined between the outer tube 16 and the cutting shaft 22 of the cutting assembly 12, and finally to the surgical site of the patient. The irrigation spacer 170 may be formed from plastic, including injection-molded plastic, but other suitable materials including, metal, ceramic, and composite materials.

The outer hub 34 may be disposed in the cavity 38 defined by the proximal portion 36 of the outer hub 34. As shown in FIGS. 2B and 3B, the outer hub 34 may have an inner hub surface 180 that tapers distally toward the axis A. Said differently, the inner hub surface 180 may have a smaller diameter at the distal end of the inner hub surface 180 and may have a larger diameter at the proximal end of the inner hub surface 180. The outer irrigation spacer surface 176 of the irrigation spacer 170 may taper distally toward the axis A. Said differently, the outer irrigation spacer surface 176 may have a smaller diameter at the distal end of the outer irrigation spacer surface 176 and may have a larger diameter at the proximal end of the outer irrigation spacer surface 176. The inner hub surface 180 and the outer irrigation spacer surface 176 may be engageable with one another to maintain a relative axial position between the outer hub 34 and the irrigation spacer 170. In a non-limiting example, that the inner hub surface 180 and the outer irrigation spacer surface 176 may be press-fit with one another. Alternatively, tapered profiles of the inner hub surface 180 and the outer irrigation spacer surface 176 may only loosely fit together, and may aid in manufacturability and/or assembly of the cutting assembly 12 of the surgical instrument 10.

In the illustrated implementation, the irrigation spacer 170 may have a hub 181 that defines the bore 174, and fins 182 extending radially away from the hub 181. The fins 182 may be spaced circumferentially about the axis A and may define the irrigation passageway 178. The irrigation spacer 170 may have two, three, four, five, six, seven, eight, or more than eight fins 182. As such, the outer irrigation spacer surface 176 may be interrupted to not extend completely circumferentially about the axis A. Other configures of the irrigation spacer 170 are contemplated to provide the irrigation passageways 178, including those without the fins 182 in the implementation. In another example, the outer irrigation spacer surface 176 may extend completely circumferentially about the axis A at the second radial distance D2 without interruption.

The outer hub 34 may have a key 184 that extends at least partially into the irrigation passageway 178 to limit rotation of the irrigation spacer 170 relative to the outer hub 34. The key 184 thus may be characterized as an anti-rotation feature. Preventing rotation between the irrigation spacer 170 and the outer hub 34 assists in maintaining alignment of the irrigation spacer 170, the outer hub 34, the outer tube 16, and the drive hub 24 to ensure proper operation of the surgical instrument. The key 184 also prevents the irrigation spacer 170 from rotating with the cutting shaft 22.

The irrigation spacer 170 may be engageable with the drive hub 24 and the irrigation spacer 170 may be configured to cooperate with the drive assembly 14 to maintain a relative axial position between the bur 82 and the distal tube opening 186. In other words, the irrigation spacer 170 may assist in spring-loading the bur 82. A thickness of the irrigation spacer 170 may be selectively designed for a given length of the cutting implement 18 to position the bur 82 at a desired distance beyond the distal tube opening 186. An internal biasing member (not identified) may be configured to urge the drive hub 24 into engagement with the irrigation spacer 170. The cutting assembly 12 may further include at least one washer 188 disposed between the irrigation spacer 170 and the drive hub 24 to assist the desired stack up. For example, the at least one washer 188 may be one, two, three washers, or four or more washers to bear against one another to control axial movement of the irrigation spacer 170 as desired.

The drive assembly 14 for the surgical instrument 10 includes the handpiece 40 extending along the axis A. The handpiece 40 includes a distal end 84 defining a distal opening 86 inwardly from the distal end 84 that is dimensioned to receive the outer hub 34 of the cutting assembly 12. The handpiece 40 also includes a proximal end 88 defining a proximal opening 90 inwardly from the proximal end 88. A back cap 92 is coupled to the handpiece 40 so as to be at least partially disposed within the proximal opening 90. A motor 94 is disposed within the handpiece 40. The motor 94 has an output shaft 96 rotatable about the axis A, and a coupling member 98 is attached to the output shaft 96 for releasably coupling the drive hub 24 of the cutting assembly 12 to the output shaft 96 such that the output shaft 96 and the drive hub 24 rotate in unison.

The drive assembly 14 also includes an irrigation port 100 coupled to the handpiece 40 and configured be removably coupled to an irrigation tube. The drive assembly 14 further includes a suction port 102 coupled to the back cap 92 and configured to be removably coupled to a suction tube. A proximal end 104 of the irrigation port 100 is positioned distal to a position where the suction port 102 is coupled to the back cap 92 so as to limit obstruction from the irrigation port 100 when coupling the suction tube to the suction port 102.

The placement of the suction port 102 and the irrigation port 100 results in the suction and irrigation tubes being spaced apart from one another. Therefore, regardless of whether the suction tube is removably coupled to the suction port 102 before or after the irrigation tube is removably coupled to the irrigation port 100, the irrigation and suction tubes are less likely to interfere with one another. Furthermore, the placement of the suction and irrigation ports 100, 102 in provides adequate clearance for a practitioner's hand 132 for ease with coupling the suction and irrigation tubes to the suction and irrigation ports 100, 102, respectively.

Figure 4:
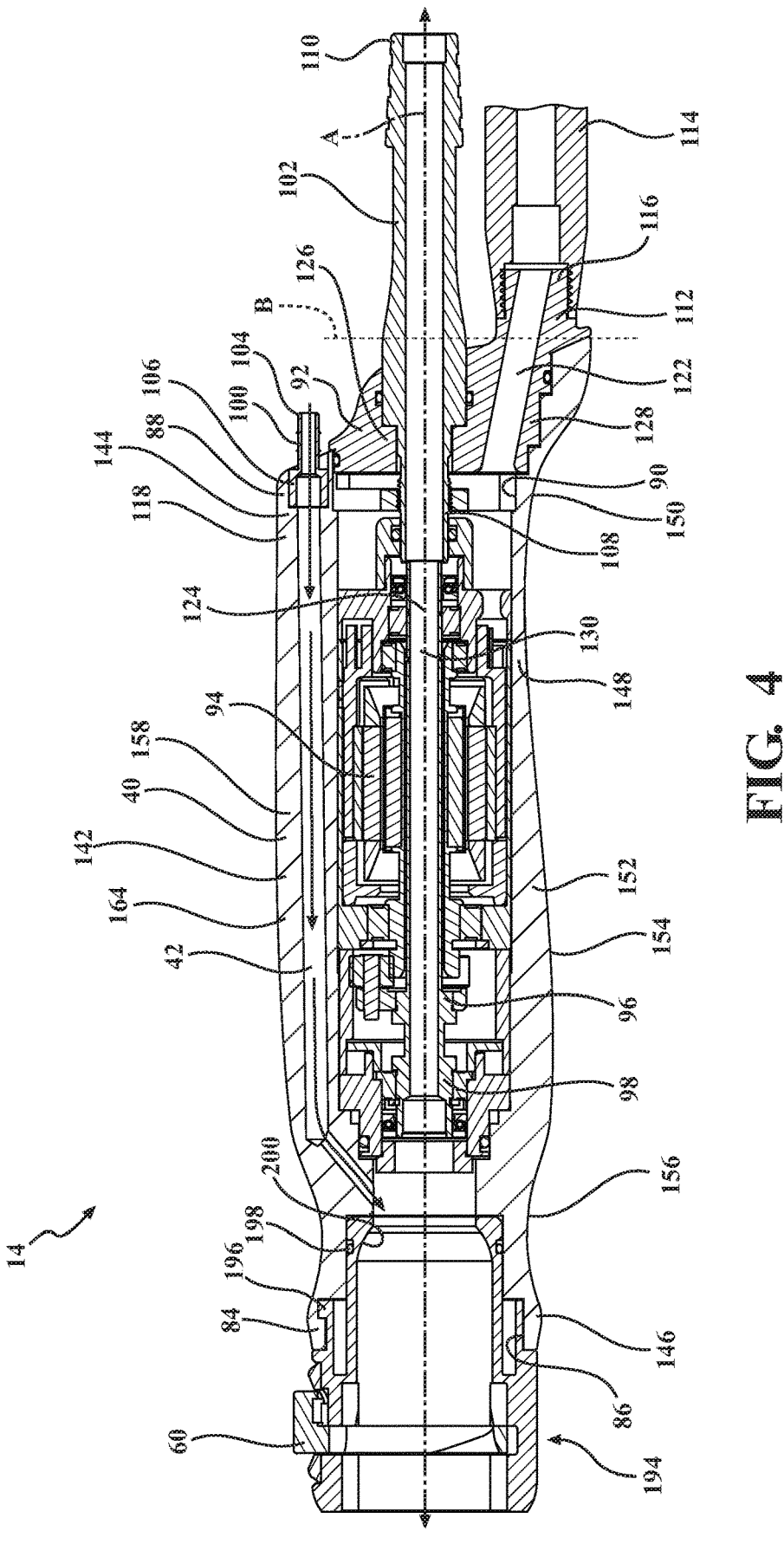
FIG. 4 is a cross-sectional view of the drive assembly of Figures and 1B. The drive assembly including an irrigation port, a suction port, and an electrical connector, and further includes contours to facilitation ergonomic handling of the surgical instrument.

In one implementation, the irrigation port 100 includes a distal end 106 coupled to the handpiece 40 and the proximal end 104 opposite the distal end 106. The suction port 102 includes a distal portion 108 disposed within and coupled to the handpiece 40. More specifically, the distal portion 108 of the suction port 102 may be disposed within and coupled to the back cap 92 of the handpiece 40. The suction port 102 also includes a proximal portion 36 extending proximally from the handpiece 40. More specifically, a proximal portion 110 of the suction port 102 may extend proximally from the back cap 92 of the handpiece 40. The proximal end 104 of the irrigation port 100 is positioned axially distal to the proximal portion 110 of the suction port 102. For convention, as shown in FIG. 4 by a dotted line B, the proximal end 104 of the irrigation port 100 may be axially distal to the proximal portion 110 of the suction port 102. Said differently, the proximal portion 110 of the irrigation port 100 may be considered to begin where the irrigation port 100 extends from the back cap 92, and the proximal portion 110 of the suction port 102 may be axially distal to where the irrigation port 100 extends from the back cap 92 (i.e., axially distal to the dotted line B in FIG. 4).

The irrigation port 100 and the suction port 102 may have a barb configuration to assist in removably coupling the irrigation and suction tubes to the irrigation and suction ports 100, 102. It is to be appreciated that a clamp or other mechanical fastener may be used to assist in removably coupling the irrigation and suction tubes to the irrigation and suction ports 100, 102.

The drive assembly 14 may further include an electrical connector 112 coupled to the handpiece 40 and configured to be coupled to a source of electrical power to power the motor 94. The source of electrical power may be a corded connection 114. The electrical connector 112 may be disposed in, or directly attached to, the back cap 92 of the handpiece 40. The electrical connector 112 may be screwed into the back cap 92 of the handpiece 40 to secure the electrical connector 112 to the drive assembly 14. Other means of coupling are contemplated, for example, press-fit, welding, or otherwise mechanically affixed to the back cap 92 of the handpiece 40. Alternatively, it is to be appreciated that the motor 94 of the surgical instrument 10 may instead be powered by a battery disposed within the surgical instrument 10.

A proximal end 116 of the electrical connector may be spaced from the proximal portion 110 of the suction port 102 such that the suction port 102 is disposed axially between the electrical connector 112 and the irrigation port 100. In other words, in order from a proximal end 118 of the surgical instrument 10 to a distal end 120 of the surgical instrument 10, the irrigation port 100, the suction port 102, and the electrical connector 112 may be spaced from one another along the axis A, respectively. The back cap 92 may at least partially define an electrical channel 122 through which electrical wires may travel to power the motor 94. It is to be appreciated that the back cap 92 may completely define the electrical channel 122. Optionally, the handpiece 40 may at least partially define the electrical channel through which the electrical power may travel to power the motor 94.

The handpiece 40 may also define the handpiece irrigation path 42 in fluid communication with the irrigation port 100 and with the proximal opening 90 of the handpiece 40 to provide irrigating fluid between the outer tube 16 and the cutting shaft 22 of the cutting assembly 12. More specifically, irrigating fluid may flow through the irrigation tube to the irrigation port 100, through the handpiece irrigation path 42 to the distal opening 86 of the handpiece 40, through the irrigation channel 48 defined between the drive hub 24 and the seal 30 of the cutting assembly 12, between the outer tube 16 and the cutting shaft 22 of the cutting assembly 12, and finally to the surgical site of the patient.

The output shaft 96 and the coupling member 98 may together define a suction flow path 124 in fluid communication with the suction port 102 to provide vacuum pressure to the drive hub 24 of the cutting assembly 12. The drive hub 24, particularly the bore 26 defined by the drive hub 24, may be in fluid communication with the cutting shaft 22, particularly the lumen 78 of the inner tube 76, to provide the vacuum pressure to the surgical site. The back cap 92 may have a suction portion 126 adjacent to the suction port 102 and an electrical portion 128 adjacent to the electrical connector 112. The suction portion 126 may be spaced from the proximal end 104 of the irrigation port 100 such that the suction portion 126 is disposed axially between the electrical portion 128 and the proximal end 104 of the irrigation port 100. The irrigation port 100, therefore, may be axially distal relative to the back cap 92. The suction port 102 may be generally aligned with the axis A and disposed at a general radial center 130 relative to the handpiece 40. The suction port 102 may be disposed at the general radial center 130 relative to the handpiece 40 to assist in removing the bits of sinus bone and tissue from the surgical site of the patient. More specifically, the suction port 102, the suction flow path 124, the drive hub 24, and the lumen of the inner tube 76 may lie in a general line parallel to the axis A through the general radial center 130 relative to the handpiece 40 to prevent clogging of the surgical instrument 10.

The lumen of the inner tube 76, the drive hub 24, the suction flow path 124, and the suction port 102 may generally increase in diameter from the distal end 120 of the surgical instrument 10 to the proximal end 118 of the surgical instrument 10. Additionally, as shown in FIG. 4, the suction port 102 may have a larger internal diameter as compared to the internal diameter of the suction flow path 124 defined by the output shaft 96. More specifically, an interface between the suction port 102 and the output shaft 96 may be sized such that the larger internal diameter of the suction port 102 as compared to the internal diameter of the suction flow path 124 defined by the output shaft 96 to further prevent clogging of the surgical instrument 10.

The irrigation port 100 may be generally aligned with the axis A and disposed radially spaced from the general radial center 130 relative to the handpiece 40. Said differently, the irrigation port 100 may extend generally parallel to the axis A. The irrigation port 100 is able to be disposed radially spaced from the general radial center 130 relative to the handpiece 40, while still allowing adequate flow of irrigating fluid to the surgical site of the patient.

The electrical connector 112 may be generally aligned with the axis A and disposed radially spaced from the general radial center 130 relative to the handpiece 40. More specifically, the suction port 102 may be spaced radially between the electrical connector 112 and the irrigation port 100. In this way, the electrical connector 112 may be spaced apart from the irrigation port 100 to avoid the irrigating fluid from interacting with the electrical power, thus avoiding damage to the surgical instrument 10.

The handpiece 40 for the surgical instrument 10 may be configured to be handled by the hand 132 including a middle finger 134, an index finger 136, a thumb 138, and a web 140 between the index finger 136 and the thumb 138. The handpiece 40 may include a handle body 142 including a proximal end 144 opposite a distal end 146. The handle body 142 may define a longitudinal axis A. The handle body 142 may also include a saddle region 148 near the proximal end 144 of the handpiece.

The saddle region 148 may define a first recess 150, may be configured to be situated upon the web 140 of the hand 132 to support the handpiece 40, and may define a lower aspect 152 of the handpiece 40 in an operative orientation. The lower aspect 152 may further include a curved surface 154 between the saddle region 148 and the distal end 146 of the handle body 142. The handle body 142 may define a second recess 156 near the distal end 146 of the handle body 142 and extending annularly about the longitudinal axis A. The second recess 156 may be configured to accommodate at least the index finger 136 and the middle finger 134 of the hand 132 in a pencil-grip arrangement in the operative orientation. The pencil-grip arrangement allows the practitioner to maneuver the handpiece 40.

The handle body 142 may further include an apex region 158 extending longitudinally between the second recess 156 and the proximal end 144. The apex region 158 assists the practitioner in handling the surgical instrument 10. It is to be appreciated that the apex region 158 extends on either side of the surgical instrument 10 to assist both left-handed and right-handed practitioners in handling the surgical instrument 10. The apex region 158 may include opposing surfaces 160, 162 that are relatively flatter than the curved surface 154 of the lower aspect 152. The opposing surfaces 160, 162 are on either side of the surgical instrument 10. The opposing surfaces 160, 162 may be angling towards and meeting one another to define an upper aspect 164 of the handpiece 40 in the operative orientation. Optionally, the handle body 142 may further define a third recess 166 extending longitudinally along at least a portion of the opposing surfaces 160, 162 and configured to provide a grip for the thumb 138 of the hand 132 in the pencil-grip arrangement.

In some implementations, the apex region 158 defines the handpiece irrigation path 42 internal to the handle body 142. Moreover, in some implementations, the handpiece 40 further includes the irrigation port 100 coupled to the apex region 158 and in fluid communication with the handpiece irrigation path 42. As shown in FIGS. 1A and 1B, the apex region 158 may be triangular in axial section, or a variety of shapes in including, but not limited to, parabolic, curvilinear, oval, and rectangular. In implementations where the handpiece 40 includes the back cap 92, the electrical connector 112 may be positioned on the back cap 92 opposite the saddle region 148 to orient the handpiece 40 in the operative orientation with the saddle region 148 supported by the hand of the user.

The drive assembly 14 may include a collet 194 coupled to the handpiece 40 and configured to receive the cutting assembly 12 to form the surgical instrument 10. The collet 194 may be unitary in construction between its ends and shaped to accommodate the outer hub 34 and the seal 30 of the cutting assembly 12. In particular, a proximal portion 200 of the collet 194 may be unitary construction to form a curved surface configured to be positioned in an abutting relationship with the proximal end 54 of the seal 30, as shown in FIGS. 2A and 2B. The abutting relationship prevents egress of irrigation fluid within the irrigation flow path. Further, the proximal portion being unitary in construction obviates the need for discrete sleeves or other subcomponents that could otherwise provide interfaces for inadvertent egress of fluid. The collet 194 may include an O-ring 198 positioned with a recess defined by the proximal portion 200 to provide an additional seal between the collet 194 and the distal opening 86 of the handpiece 40.

The collet 194 may be coupled to the handpiece 40 with engagement tabs 196 (one shown) with complementary slots defined by the handpiece. 40. The tabs 196 may be two tabs that subtend different length arcs, wherein the slots similarly subtend complementary arcs. The arrangement requires the collet 194 be engaged with the handpiece 40 in a single orientation such that a button 168 of the latching mechanism 60 is aligned radially with the upper aspect 164 of the handpiece 40 in the operative orientation. To assemble the collet 194 with the handpiece 40 the engagement tabs 196 are inserted through the corresponding slots, and the collet 194 is rotated into a locked position. The tabs-in-slots arrangement obviates the need for set screws, which may further obviate the need for sealant over the holes through which the set screws are disposed. Another exemplary collet is disclosed in commonly-owned U.S. Pat. No. 7,237,990 issued Jul. 3, 2007, the entire contents of which are hereby incorporated by reference.

The foregoing disclosure is not intended to be exhaustive or limit the invention to any particular form. The terminology which has been used is intended to be in the nature of words of description rather than of limitation. Many modifications and variations are possible in light of the above teachings and may be practiced other than as specifically described. It will be further appreciated that the terms "include," "includes," and "including" have the same meaning as the terms "comprise," "comprises," and "comprising."

The invention claimed is:

1. A cutting assembly for a surgical instrument including a drive assembly, and a handpiece defining a handpiece irrigation path, the cutting assembly comprising:

an outer hub;

an outer tube extending from the outer hub;

a cutting implement comprising a cutting shaft rotatably disposed within the outer tube, and a distal cutting end, wherein an irrigation flow path is defined between the outer tube and the cutting shaft; and a drive hub coupled to the cutting shaft and configured to be removably coupled with the drive assembly, wherein the drive hub comprises a retention flange positioned to permit fluid to flow from the handpiece irrigation path to the irrigation flow path with the drive hub removably coupled to the drive assembly of the surgical instrument, and to limit proximal movement of the cutting shaft relative to the outer tube with the cutting assembly decoupled from the drive assembly of the surgical instrument, wherein the outer hub defines a cavity, and an irrigation aperture through which the cutting shaft extends into the cavity, and wherein a distal end of the drive hub is positioned within the cavity and configured to be spaced apart from the irrigation aperture by a gap defined by an inner surface of the outer hub and an outer surface of the drive hub with the drive hub removably coupled to the drive assembly of the surgical instrument such that fluid is permitted to flow through the gap and the irrigation aperture and into the irrigation flow path.

2. The cutting assembly of claim 1, wherein an outer diameter of the drive hub is greater than an outer diameter of the irrigation aperture.

3. The cutting assembly of claim 1, wherein the cutting shaft defines a lumen, and wherein the drive hub defines a bore in fluid communication with the lumen such that irrigation and suction are separated by the drive hub.

4. The cutting assembly of claim 1, further comprising a seal coupled to the outer hub, wherein the retention flange is configured to contact the seal to limit the proximal movement.

5. The cutting assembly of claim 4, wherein the seal has an inner retention flange, and wherein the retention flange of the drive hub has an outer dimension greater than an innermost diameter of the inner retention flange.

6. The cutting assembly of claim 5, wherein the retention flange is positioned distal to the seal with the drive hub removably coupled to the drive assembly of the surgical instrument.

7. The cutting assembly of claim 4, wherein the seal comprises a locking tab engageable with a groove defined by the outer hub.

8. The cutting assembly of claim 1, further comprising an irrigation spacer coupled to the outer hub and positioned distal to the drive hub, the irrigation spacer defining a bore through which the cutting shaft is rotatably disposed, and further defining irrigation passageways.

9. The cutting assembly of claim 8, wherein the irrigation spacer comprises a hub defining the bore, and fins extending radially from the hub to define the irrigation passageways therebetween.

10. The cutting assembly of claim 9, wherein the outer hub comprises a key positioned between an adjacent pair of the fins to prevent rotation of the irrigation spacer relative to the outer hub.

11. The cutting assembly of claim 9, wherein the fins are spaced circumferentially about the hub.

12. The cutting assembly of claim 8, wherein the irrigation spacer is configured to axially separate a distal surface of the drive hub from the irrigation aperture to provide clearance for the fluid to flow.

13. A cutting assembly for a surgical instrument including a drive assembly, and a handpiece defining a handpiece irrigation path, the cutting assembly comprising:

an outer hub defining a cavity and an irrigation aperture in fluid communication with the cavity;

an outer tube extending from the outer hub;

a seal coupled to the outer hub and at least partially disposed within the cavity;

a cutting implement comprising a cutting shaft extending through the irrigation aperture and rotatably disposed within the outer tube, and a distal cutting end; and a drive hub coupled to a proximal end of the cutting shaft and comprising a retention flange, wherein the drive hub is configured to be removably coupled with the drive assembly, wherein the drive hub is axially movable within the cavity between a first position in which the retention flange is positioned distal to the seal and a distal end of the drive hub is spaced apart from the irrigation aperture by a gap defined by an inner surface of the outer hub and an outer surface of the drive hub such that fluid is permitted to flow through the cavity, between the retention flange and the seal, through the gap, and into the irrigation aperture, and a second position in which the retention flange is contacting the seal.

14. The cutting assembly of claim 13, wherein the seal has an innermost diameter, and wherein the retention flange has an outer dimension greater than the innermost diameter so as to contact the seal in the second position.

15. The cutting assembly of claim 13, wherein the retention flange is positioned distal to the seal with the drive hub in the first position.

16. The cutting assembly of claim 13, wherein the cutting shaft defines a lumen, and wherein the drive hub defines a bore in fluid communication with the lumen such that irrigation and suction are separated by the drive hub in the first position.

17. The cutting assembly of claim 13, further comprising an irrigation spacer coupled to the outer hub and positioned distal to the seal, the irrigation spacer defining a bore through which the cutting shaft is rotatably disposed, and further defining irrigation passageways.

18. The cutting assembly of claim 17, wherein the irrigation spacer comprises a hub defining the bore, and fins extending radially from the hub to define the irrigation passageways therebetween.

19. A cutting assembly for a surgical instrument including a drive assembly, and a handpiece defining a handpiece irrigation path and a suction flow path, the cutting assembly comprising:

an outer hub defining a cavity;

an outer tube extending from the outer hub;

a cutting implement comprising a cutting shaft rotatably disposed within the outer tube, and a distal cutting end, the cutting shaft defining a lumen; and a drive hub coupled to the cutting shaft and disposed within the cavity, wherein the drive hub is configured to be removably coupled with the drive assembly to rotate the cutting shaft within the outer tube, the drive hub comprising a retention flange and defining a bore in fluid communication with the lumen of the cutting shaft, wherein the lumen and the bore are configured to be arranged in fluid communication with the suction flow path of the handpiece; and a seal coupled to the outer hub and at least partially disposed within the cavity, wherein the outer hub further defines an irrigation aperture through which the cutting shaft extends into the cavity, wherein the retention flange is configured to be spaced apart from a distal end of the seal and a distal end of the drive hub is configured to be spaced apart from the irrigation aperture by a gap defined by an inner surface of the outer hub and an outer surface of the drive hub with the drive hub removably coupled to the drive assembly of the surgical instrument such that fluid is permitted to flow from the handpiece irrigation path through the cavity between the drive hub and the seal such that irrigation and suction are separated by the drive hub.

\* \* \* \* \*